(12) United States Patent
Wilcox (10) Patent No.: US 12,263,287 B2
(45) Date of Patent: Apr. 1, 2025

(54) DISPOSABLE CASSETTE CONDITIONING SYSTEM AND METHOD

(71) Applicants: BAXTER INTERNATIONAL INC., Deerfield, IL (US); BAXTER HEALTHCARE SA, Glattpark (CH)

(72) Inventor: Matthew David Wilcox, Cary, IL (US)

(73) Assignees: Baxter International Inc., Deerfield, IL (US); Baxter Healthcare SA, Glattpark (CH)

(*) Notice: Subject to any disclaimer, the term of this patent is extended or adjusted under 35 U.S.C. 154(b) by 1196 days.

(21) Appl. No.: 16/460,214

(22) Filed: Jul. 2, 2019

(65) Prior Publication Data

US 2020/0009311 A1    Jan. 9, 2020

Related U.S. Application Data

(60) Provisional application No. 62/693,696, filed on Jul. 3, 2018.

(51) Int. Cl.
*A61M 1/28* (2006.01)
*A61M 1/14* (2006.01)
*G01M 3/28* (2006.01)

(52) U.S. Cl.
CPC .......... *A61M 1/288* (2014.02); *A61M 1/1522* (2022.05); *A61M 1/1524* (2022.05);
(Continued)

(58) Field of Classification Search
None
See application file for complete search history.

(56) References Cited

U.S. PATENT DOCUMENTS 5,350,357 A * 9/1994 Kamen ............... A61M 1/1524
   604/29
6,302,653 B1 * 10/2001 Bryant .................... F04B 51/00
   417/63

(Continued)

FOREIGN PATENT DOCUMENTS

EP    1 680 155 B1    2/2012

OTHER PUBLICATIONS

Written Opinion of the International Searching Authority mailed Oct. 17, 2019 in corresponding PCT Application No. PCT/US2019/040305—5 Pages.

(Continued)

*Primary Examiner* — Jonathan M Peo
(74) *Attorney, Agent, or Firm* — K&L Gates LLP (57) ABSTRACT

A medical fluid delivery system comprises: (i) a medical fluid delivery machine including a pneumatic manifold having pump and valve actuation areas and a pumping gasket overlaying the pump and valve actuation areas, sources of positive and negative pneumatic pressure, plural pneumatic valves located between the pneumatic sources and the pump and valve actuation areas, and a control unit in operable communication with the plural pneumatic valves; and (ii) a disposable cassette including a fluid pump chamber that aligns with the pump actuation area when the disposable cassette is mated with the pneumatic manifold, the disposable cassette including sheeting overlaying the fluid pump chamber, wherein the control unit is configured to operate the pneumatic valves to perform a conditioning routine that moves the pumping gasket and the cassette sheeting while mated in an attempt to remove small air pockets from between the pumping gasket and the cassette sheeting.

18 Claims, 7 Drawing Sheets

(52) U.S. Cl.
CPC .......... *A61M 1/155* (2022.05); *A61M 1/1565* (2022.05); *A61M 1/159* (2022.05); *A61M 1/281* (2014.02); *G01M 3/2869* (2013.01); *A61M 1/156* (2022.05); *A61M 2205/07* (2013.01); *A61M 2205/12* (2013.01); *A61M 2209/02* (2013.01)

(56) References Cited

U.S. PATENT DOCUMENTS

| | | | |
|---|---|---|---|
| 2008/0202591 A1* | 8/2008 | Grant | A61M 1/154 137/12 |
| 2011/0239742 A1 | 10/2011 | Mueller et al. | |
| 2012/0083729 A1* | 4/2012 | Childers | A61M 1/154 73/714 |
| 2012/0123322 A1* | 5/2012 | Scarpaci | A61M 1/288 250/573 |

OTHER PUBLICATIONS

International Search Report mailed Oct. 17, 2019 in corresponding PCT Application No. PCT/US2019/040305—3 Pages.

* cited by examiner

DISPOSABLE CASSETTE CONDITIONING SYSTEM AND METHOD

RELATED APPLICATIONS

This application claims the benefit of and priority to U.S. Provisional Patent Application No. 62/693,696 filed Jul. 3, 2018, entitled "DISPOSABLE CASSETTE CONDITIONING SYSTEM AND METHOD," which is incorporated herein by reference in its entirety.

BACKGROUND

The present invention relates generally to medical fluid systems and more particularly to the testing and setup of such systems, and in particular pneumatically driven peritoneal dialysis systems, such as hemodialysis or periotneal dialysis.

It is known in peritoneal dialysis systems to perform integrity tests prior to treatment, including "wet" integrity tests and "dry" integrity tests. "Wet" integrity tests attempt to verify that the numerous fluid valves in a disposable cassette do not leak, that leaks do not occur between multiple pump chambers in the cassette, that leaks do not occur across fluid pathways, and that an isolation occluder, which is intended to stop liquid flow in fluid lines connected to the cassette in the event of a system malfunction, is performing that procedure properly. In one known wet leak test described in U.S. Pat. No. 5,350,357, a disposable cassette is loaded into a peritoneal dialysis cycler and the solution bags are connected. The test consists of the following steps:
  (i) a negative pressure decay test of the fluid valve diaphragms is performed;
  (ii) a positive pressure decay test of the fluid valve diaphragms is performed;
  (iii) a positive pressure decay test is performed on the first pump chamber, while a negative pressure decay test is performed on the second pump chamber;
  (iv) a negative pressure decay test is performed on the first pump chamber, while a positive pressure decay test is performed on the second pump chamber; after which
  (v) both pump chambers are filled with a measured volume of fluid, all fluid valves are opened and the occlude is closed, positive pressure is applied to both pump chambers for a period of time, after which the volume of fluid in each pump chamber is measured again to determine if any fluid has leaked across the occlude.

As indicated, the above testing procedure is performed after solution bags are connected to the peritoneal dialysis system. If integrity of the cassette or tubing is faulty, the sterility of the solution bags becomes compromised. In such a case, both the disposable cassette and solution bags have to be discarded. Additionally, it is possible that liquid from the solution bags can be sucked into the machine's actuation system, causing the actuation system of the machine to malfunction.

Wet tests are also susceptible to false triggers. In particular, cold solution used in the wet test causes false disposable integrity test alarms each year because the tests fail when an occlude, which is supposed to clamp off all fluid lines, does not properly crimp or seal the tubing lines. When the solution is cold, it cools the set tubing to a lower temperature than the tubing would be if placed only in room air. Colder tubing is harder to occlude, allowing fluid in some cases to leak past the occluder and cause the test to fail. Once a dialysis therapy starts, the fluid passing through the tubing is warmed to about 37° C., enabling the occluder to perform satisfactorily.

A "dry" integrity test is described briefly in U.S. Pat. No. 6,302,653, the entire contents of which are incorporated herein by reference and relied upon. The description is based in part upon the "dry test" implemented in the Baxter HomeChoice® cycler in December of 1998. That test consisted of four steps, the first of which occurred before the solution bags were connected. The next three steps required the solution bags to be connected but did not require fluid to be pulled from the bags into the machine. The "dry" test eliminated the problem of fluid potentially leaking into the pneumatics of the machine. The test did not prevent the sterility of the bags from being compromised potentially upon a leak and thus from being discarded if the integrity of the disposable cassette was compromised.

One primary portion of a dry integrity test for a Baxter HomeChoice® cycler or a Baxter Amia® cycler involves monitoring a leak rate of air between its pumping gasket and the sheeting of the disposable cassette when the cassette is mounted to the machine or cycler. The test basically determines whether the pumping gasket and the cassette sheeting are mated properly and may fail often especially when (i) there are deformities or imperfections in either one or both of the gasket or sheeting and/or (ii) there is misalignment between same.

A need exists accordingly to help the pumping gasket and the cassette sheeting to seal together better to reduce the amount of dry integrity test errors due to a faulty interface between the sheeting of the disposable cassette to the gasket of pneumatic pumping actuator.

SUMMARY

The examples described herein disclose systems and methods to improve a peritoneal dialysis ("PD") treatment. It should be appreciated however that the systems and methods are applicable to any type of medical fluid delivery machine in which a pneumatic actuator includes a membrane gasket that is mated with and sealed to sheeting of a disposable cassette. Such medical fluid delivery machine could be any of peritoneal dialysis ("PD"), plasmapherisis, hemodialysis ("HD"), hemofiltration ("HF") hemodiafiltration ("HDF"), continuous renal replacement therapy ("CRRT"), apheresis, autotransfusion, hemofiltration for sepsis, and extracorporeal membrane oxygenation ("ECMO") treatments. These modalities may be referred to collectively or generally individually herein as medical fluid delivery system(s).

In one embodiment, the medical fluid delivery machine or PD cycler includes electrically actuated pneumatic valves that are under control of a control unit having processing and memory, wherein the memory stores software configured to cause the pneumatic valves to be operated so that they cause negative and/or positive pressure to be applied to the pumping gasket after it has been mated with the sheeting of the disposable cassette. The negative and positive pressure is applied either before or after a dry integrity test in an effort to improve the seal between the pumping gasket and cassette sheeting. The massaging and moving of the gasket and sheet while together helps to squeeze or ring air pockets out from between the gasket and sheet. The massaging and moving of the gasket and sheet while together also helps one of the gasket or sheeting to comply with and imperfection of the other of the gasket or sheeting. The massaging and moving of the gasket and sheet also helps with misalignment between same. All benefits help to reduce the error rate in a subsequent dry integrity test.

In an embodiment, pneumatic valves are provided for: (i) controlling fluid flow to and from a heater, (ii) controlling fluid flow to a drain, (iii) controlling fluid flow to and from a patient, (iv) controlling air flow to a vent from a first reference chamber, (v) controlling air flow between the first reference chamber and a first pump chamber, (vi) controlling negative pneumatic pressure between a negative pneumatic storage tank and the first pump chamber, (vii) controlling positive pneumatic pressure between a positive pneumatic storage tank and the first pump chamber, (viii) controlling fluid flow between the first pump chamber and the heater bag or drain, (ix) controlling fluid flow between the first pump chamber and the patient or supply containers, (x) controlling fluid flow between a second pump chamber and the patient or supply containers, (xi) controlling fluid flow between the second pump chamber and the heater bag or drain, (xii) controlling positive pneumatic pressure between the positive pneumatic storage tank and the second pump chamber, (xiii) controlling negative pneumatic pressure between the negative pneumatic storage tank and the second pump chamber, (xiv) controlling air flow between a second reference chamber and the second pump chamber, (xv) controlling air flow to a vent from a second reference chamber, (xvi) controlling fluid flow between a first supply container and the pump chambers, (xvii) controlling fluid flow between a second supply container and the pump chambers, (xviii) controlling fluid flow between a third supply container and the pump chambers, (xix) controlling fluid flow between a fourth supply container and the pump chambers, and (xx) controlling fluid flow between a fifth supply container and the pump chambers.

In a first step of one embodiment for a pumping gasket and cassette conditioning algorithm or routine stored in software and executed by a processor of the control unit of a medical fluid deliver machine, such as a peritoneal dialysis cycler, the control unit causes the two pneumatic vent valves to open while all other eighteen pneumatic valves are closed. This first step vents the reference chambers, which are known volume chambers used to measure the pressure in the pump chambers and in combination with the control unit to determine a volume of medical fluid pulled into or expelled from the pump chambers using Boyle's Law. The pressure in the reference chambers at the end of the first step is zero or close to zero psig.

In a second step of one embodiment for a pumping gasket and cassette sheeting conditioning algorithm or routine stored in software and executed by a processor of the control unit of a medical fluid deliver machine, such as a peritoneal dialysis cycler, the control unit causes all pneumatic valves to open except for (i) the pneumatic valves between the positive pneumatic storage tank and the first and second pump chambers and (ii) the pneumatic valves between the first and second pump chambers and the first and second reference chambers. The two pneumatic vent valves to the reference chambers are still open, so that the reference chamber pressures are still at atmospheric pressure. The pneumatic valves between the negative pneumatic storage tank and the first and second pump chambers are opened to allow negative pressure to be applied to the pump chambers, pulling the pumping gasket and cassette sheeting together into pump chamber halves defined by a pneumatic manifold of the machine or cycler. All fluid valves are opened in one implementation to allow air to flow into the disposable cassette to reduce or eliminate negative pressure from building within the cassette that could potentially resist the movement of the cassette sheeting. The pumping gasket and the cassette sheeting are thereby free to move and stretch and condition together to (i) help remove small gaps or air pockets in the sealing between the pumping gasket and the cassette sheeting, e.g., due to imperfections in either one or both of the gasket or sheeting and (ii) help align the cassette to the pneumatic manifold of the machine.

In a third step of one embodiment for a pumping gasket and cassette sheeting conditioning algorithm or routine stored in software and executed by a processor of the control unit of a medical fluid deliver machine, such as a peritoneal dialysis cycler, the control unit causes all pneumatic valves to be closed except for (i) the pneumatic valves between the positive pneumatic storage tank and the first and second pump chambers and (ii) the pneumatic vent valves to the reference chambers, so that the reference chamber pressures are maintained at atmospheric pressure. The pneumatic valves opened between the positive pneumatic storage tank and the first and second pump chambers allow positive pressure to be applied to the pump chambers, pushing the pumping gasket and cassette sheeting together into pump chamber halves defined by the disposable cassette. All fluid valves are closed in one implementation to allow positive pressure to build inside the disposable cassette, so that positive pressure is applied to both sides of the mated gasket and cassette sheeting to (i) squeeze air out small gaps or air pockets residing between the pumping gasket and the cassette sheeting and (ii) help align the cassette to the pneumatic manifold of the machine.

The control unit having processing running software for the conditioning algorithm may be programmed to repeat steps two and three one or more time in various embodiments. Also, steps two and three have been described as operating the first and second pump chambers in the same manner. Alternatively or additionally, the gasket and sheeting at one pump chamber may be placed under negative pressure, while the gasket and sheeting at the other pump chamber is placed under positive pressure.

In a fourth step of one embodiment for a pumping gasket and cassette sheeting conditioning algorithm or routine stored in software and executed by a processor of the control unit of a medical fluid deliver machine, such as a peritoneal dialysis cycler, the control unit causes all pneumatic valves to be closed except for (i) the pneumatic valves between the first and second pump chambers and the first and second reference chambers and (ii) the pneumatic vent valves to the reference chambers, so that the positive pressure built in the third step is vented to atmosphere.

In a fifth step of one embodiment for a pumping gasket and cassette sheeting conditioning algorithm or routine stored in software and executed by a processor of the control unit of a medical fluid deliver machine, such as a peritoneal dialysis cycler, the control unit causes the two pneumatic vent valves to be open while all other eighteen pneumatic valves are closed. This valve at rest configuration is the same as the configuration of the first step.

As mentioned above, the positive and negative pressure conditioning of the gasket and cassette sheeting may be performed either before or after a dry integrity test. For example, in one instance, the conditioning routine is provided before the dry integrity test. The first to the fifth steps described above are performed. Afterwards, the dry integrity test is performed.

In another example, the conditioning routine is provided after experiencing a dry integrity test failure. The control unit is programmed such that after the dry integrity test failure, the medical fluid delivery machine, such as a peritoneal dialysis cycler, prompts the patient or caregiver the press a "resume" button acknowledging the dry integrity test failure. Once "resume" is pressed, the first to the fifth steps described above are performed. Afterwards, the dry integrity test is performed again. This second example may be performed in combination with the first example or in place of the first example.

The benefits of the conditioning routine are not limited to helping the dry integrity testing. In a third example, the conditioning routine is performed as a result of a slow flow error (e.g., medical fluid is pumped to or from the patient too slowly despite attempting a higher flowrate). The control unit is programmed such that after the slow flow error, the medical fluid delivery machine, such as a peritoneal dialysis cycler, prompts the patient or caregiver the press a "resume" button acknowledging the slow flow error. Once "resume" is pressed, the first to the fifth steps described above are performed. Afterwards, the treatment resumes with hopefully a better seal between the pumping gasket and the cassette sheeting. This third example may be performed in combination with either one or both the first example and/or the second example.

Other tests, errors or alerts that may be aided by the conditioning routine of the present disclosure include any that involve actuation of the pumping gasket and the cassette sheeting. It should be appreciated that in any of the situations in which the conditioning routine is performed in response to an error or alert, a patient or caregiver action, such as the pressing of a "resume" button is not necessary. For example, if treatment is performed at night while the patient sleeps, it may be desirable not to wake the patient and instead perform the conditioning steps described above automatically.

In light of the disclosure herein and without limiting the disclosure in any way, in a first aspect of the present disclosure, which may be combined with any other aspect listed herein unless specified otherwise, a medical fluid delivery system comprises: a medical fluid delivery machine including a pneumatic manifold having pump and valve actuation areas and a pumping gasket overlaying the pump and valve actuation areas, a source of positive pneumatic pressure, a source of negative pneumatic pressure, plural pneumatic valves located between the sources of positive and negative pneumatic pressure and the pump and valve actuation areas, and a control unit in operable communication with the plural pneumatic valves; and a disposable cassette including a fluid pump chamber that aligns with the pump actuation area when the disposable cassette is mated with the pneumatic manifold, the disposable cassette including sheeting overlaying the fluid pump chamber, wherein the control unit is configured to operate the pneumatic valves to perform a conditioning routine that moves the pumping gasket and the cassette sheeting while mated in an attempt to remove small air pockets from between the pumping gasket and the cassette sheeting.

In a second aspect of the present disclosure, which may be combined with any other aspect listed herein unless specified otherwise, the control unit is further configured to perform an integrity test to determine if the pumping gasket and the cassette sheeting are adequately sealed together, and wherein the conditioning routine is performed prior to the integrity test.

In a third aspect of the present disclosure, which may be combined with any other aspect listed herein unless specified otherwise, the control unit is further configured to perform an integrity test to determine if the pumping gasket and the cassette sheeting are adequately sealed together, and wherein the conditioning routine is performed after a failure of the integrity test.

In a fourth aspect of the present disclosure, which may be combined with the third aspect in combination with any other aspect listed herein unless specified otherwise, the control unit is further configured to perform a second integrity test after the conditioning routine is performed.

In a fifth aspect of the present disclosure, which may be combined with any other aspect listed herein unless specified otherwise, the control unit is further configured to monitor for a slow flow condition, and wherein the conditioning routine is performed after the detection of the slow flow condition.

In a sixth aspect of the present disclosure, which may be combined with any other aspect listed herein unless specified otherwise, moving the pumping gasket and the cassette sheeting while mated during the conditioning routine includes (i) applying negative pneumatic pressure to the pumping gasket and the cassette sheeting while fluid valves of the disposable cassette are open and (ii) applying positive pneumatic pressure to the pumping gasket and the cassette sheeting while the fluid valves of the disposable cassette are closed.

In a seventh aspect of the present disclosure, which may be combined with the sixth aspect in combination with any other aspect listed herein unless specified otherwise, the conditioning routine includes repeating (i) and (ii) at least one time.

In an eighth aspect of the present disclosure, which may be combined with any other aspect listed herein unless specified otherwise, the pump actuation area and the fluid pump chamber are first chambers, wherein the pneumatic manifold includes a second pump actuation area that mates with a second fluid pump chamber, and wherein the conditioning routine includes (i) applying negative pneumatic pressure to the first and second mated pump actuation and fluid pump chambers simultaneously and (ii) applying positive pneumatic pressure to the first and second mated pump actuation and fluid pump chambers simultaneously.

In a ninth aspect of the present disclosure, which may be combined with any other aspect listed herein unless specified otherwise, the pump actuation area and the fluid pump chamber are first chambers, wherein the pneumatic manifold includes a second pump actuation area that mates with a second fluid pump chamber, and wherein the conditioning routine includes applying negative pneumatic pressure to the first mated pump actuation area and fluid pump chamber while applying positive pneumatic pressure to the second mated pump actuation area and fluid pump chamber.

In a tenth aspect of the present disclosure, which may be combined with any other aspect listed herein unless specified otherwise, the pumping gasket and the cassette sheeting are pre-domed towards the pump actuation area.

In an eleventh aspect of the present disclosure, which may be combined with any other aspect listed herein unless specified otherwise, a medical fluid delivery system comprises: a medical fluid delivery machine including a pneumatic manifold having a pump actuation area and a pumping gasket overlaying the pump actuation area; a disposable cassette including a fluid pump chamber that aligns with the pump actuation area when the disposable cassette is mated with the pneumatic manifold, the disposable cassette including sheeting overlaying the fluid pump chamber; and which is configured to perform a conditioning routine that moves the pumping gasket and the cassette sheeting while mated in two directions to remove small air pockets from between the pumping gasket and the cassette sheeting, the conditioning routine performed (i) prior to or in response to a result of a disposable cassette installation test or (ii) in response to a treatment error or alert.

In a twelfth aspect of the present disclosure, which may be combined with the eleventh aspect in combination with any other aspect listed herein unless specified otherwise, the disposable cassette installation test includes a dry integrity test.

In a thirteenth aspect of the present disclosure, which may be combined with the eleventh aspect in combination with any other aspect listed herein unless specified otherwise, the treatment error or alert includes a slow flow error.

In a fourteenth aspect of the present disclosure, which may be combined with the eleventh aspect in combination with any other aspect listed herein unless specified otherwise, the medical fluid delivery machine is configured to perform a conditioning routine by pneumatically pulling the mated pumping gasket and cassette sheeting in a first one of the two directions and by pneumatically pushing the mated pumping gasket and cassette sheeting in a second one of the two directions.

In a fifteenth aspect of the present disclosure, which may be combined with the fourteenth aspect in combination with any other aspect listed herein unless specified otherwise, the disposable cassette is in fluid communication with a plurality of fluid lines, and wherein the fluid lines are open when pneumatically pulling the mated pumping gasket and cassette sheeting and occluded when pneumatically pushing the mated pumping gasket and cassette sheeting.

In a sixteenth aspect of the present disclosure, which may be combined with the eleventh aspect in combination with any other aspect listed herein unless specified otherwise, the pumping gasket includes at least one aperture positioned and arranged to enable negative pneumatic pressure to be applied through the aperture to pull the cassette sheeting against the pumping gasket.

In a seventeenth aspect of the present disclosure, which may be combined with the eleventh aspect in combination with any other aspect listed herein unless specified otherwise, the medical fluid delivery machine includes a control unit, the control unit configured to cause the conditioning routine to be performed.

In an eighteenth aspect of the present disclosure, which may be combined with any other aspect listed herein unless specified otherwise, a method for a medical fluid delivery machine including a pumping gasket that mates with sheeting of a disposable cassette when the disposable cassette is mounted to the medical fluid delivery machine is provided, the method including: conditioning the pumping gasket and cassette sheeting when mated by moving the pumping gasket and cassette sheeting together in an attempt to remove small air pockets from between the pumping gasket and the cassette sheeting; and performing an integrity test on the conditioned pumping gasket and cassette sheeting to evaluate how well the cassette sheeting is sealed to the pumping gasket.

In a nineteenth aspect of the present disclosure, which may be combined with the eighteenth aspect in combination with any other aspect listed herein unless specified otherwise, the conditioning includes moving the mated pumping gasket and cassette sheeting back and forth at least one time.

In a twentieth aspect of the present disclosure, which may be combined with the eighteenth aspect in combination with any other aspect listed herein unless specified otherwise, the method includes conditioning the pumping gasket and cassette sheeting again upon at least one of: (i) a failure of the integrity test or (ii) a slow flow error during a treatment provided by the medical fluid delivery machine and the disposable cassette.

In a twenty-first aspect of the present disclosure, any of the structure and functionality disclosed in connection with FIGS. 1 to 7 may be included or combined with any of the other structure and functionality disclosed in connection with FIGS. 1 to 7.

In light of the present disclosure and the above aspects, it is therefore an advantage of the present disclosure to provide an improved medical fluid delivery system and method, such as peritoneal dialysis ("PD"), system and method.

It is another advantage of the present disclosure to provide a medical fluid delivery system and method having a pumping gasket and cassette sheeting conditioning routine that helps to reduce or respond to dry integrity test failures.

It is a further advantage of the present disclosure to provide a medical fluid delivery system and method having a pumping gasket and cassette sheeting conditioning routine that helps to reduce or respond to slow flow errors.

It is still another advantage of the present disclosure to provide a medical fluid delivery system and method having a pumping gasket and cassette sheeting conditioning routine that is time efficient to run.

The advantages discussed herein may be found in one, or some, and perhaps not all of the embodiments disclosed herein. Additional features and advantages are described herein, and will be apparent from, the following Detailed Description and the figures.

DETAILED DESCRIPTION

System Overview

Figure 1:
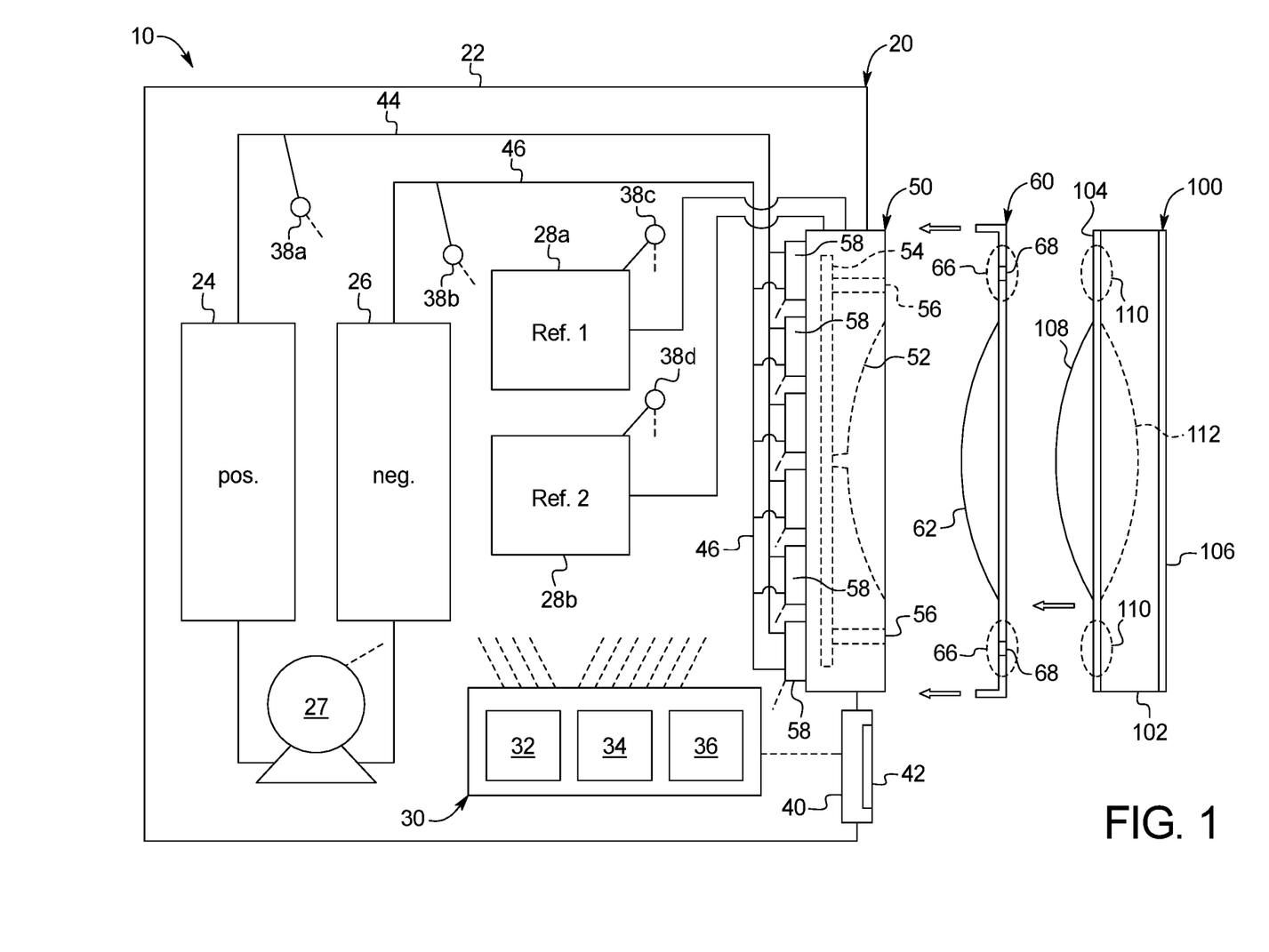
FIG. 1 is a schematic view of one embodiment of a system employing the conditioning routines of the present disclosure.

Referring now to the drawings and in particular to FIG. 1, a medical fluid delivery system, such as a peritoneal dialysis system 10 is illustrated. While system 10 is illustrated in the context of peritoneal dialysis ("PD"), the teachings herein are applicable to any medical fluid delivery system in which a machine operates with a disposable set including a disposable cassette, including but not limited to peritoneal dialysis ("PD"), plasmapherisis, hemodialysis ("HD"), hemofiltration ("HF") hemodiafiltration ("HDF"), continuous renal replacement therapy ("CRRT"), apheresis, autotransfusion, hemofiltration for sepsis, extracorporeal membrane oxygenation ("ECMO") treatments, and medical delivery. These modalities may be referred to collectively or generally individually herein as medical fluid delivery system(s).

System 10 includes a medical fluid delivery machine 20, such as a PD cycler. One suitable cycler and disposable set operating with the cycler is disclosed in U.S. Pat. No. 9,248,225, describing Baxter's Amia® cycler, the entire contents of which are incorporated herein by reference and relied upon. FIG. 1 illustrates schematically one embodiment for providing pneumatic actuation to the disposable set. In particular, medical fluid delivery machine 20 includes a housing 22 that holds a positive pneumatic pressure source 24 and a negative pneumatic pressure source 26, which may each be charged to a desired pneumatic pressure via a pneumatic pump 27 under the control of a control unit 30. Control unit 30 includes one or more processor 32, one or more memory 34, and a video controller 36 which outputs to a video screen 42 of a user interface 40. User interface 40 may also include a touch screen overlay (not illustrated) and/or one or more electromechanical switch (not illustrated), such as a membrane switch for inputting information into control unit.

Positive pneumatic pressure source 24 and a negative pneumatic pressure source 26 supply positive and negative pneumatic pressure respectively to a pneumatic manifold 50. Pneumatic manifold 50 as illustrated in more detail in FIG. 37 of U.S. Pat. No. 9,248,225 and includes or defines a pumping chamber or area 52 and a plurality of pneumatic channels, indicated generally by channel bar 54 within pneumatic manifold 50. Pneumatic manifold 50 may be made of metal, e.g., aluminum, or plastic, e.g., injection molded. Pneumatic channels 54 lead to pumping chamber or area 52 and to a plurality of valve channels or areas 56.

In the illustrated embodiment, a plurality of electrically actuated pneumatic valves 58 are mounted to the back or inner side of pneumatic manifold 50. In the illustrated embodiment, a positive pneumatic line 44 leads from positive pneumatic pressure source 24 to each of pneumatic valves 58, and a negative pneumatic line 46 leads from negative pneumatic pressure source 24 to each of the pneumatic valves. In one embodiment, each valve of a disposable cassette 100 operating with medical fluid delivery machine 20 is opened under negative pressure and closed under positive pressure, thus each corresponding pneumatic valve 58 is supplied with both positive and negative pressure. In an alternative embodiment, the valves of disposable cassette may be biased for example to close automatically when depressurized and to open upon negative pressure. Here, the corresponding pneumatic valves 58 would only need to be supplied with negative pneumatic pressure. The pump chambers of disposable cassette 100 pull fluid into the cassette via negative pneumatic pressure and push fluid from the cassette under positive pressure. The corresponding pneumatic valves 58 for the pump chambers therefore have both positive and negative pneumatic pressure supplies in one embodiment.

As illustrated in FIG. 1, references chambers 28a and 28b are provided, one for each of two pump chambers. References chambers 28a and 28b are known volume chambers used to measure the pressure in the pump chambers and in combination with control unit 30 to determine a volume of medical fluid pulled into or expelled from the pump chambers using Boyle's Law. In the illustrated embodiment, positive pneumatic line 44 is provided with a first pressure sensor 38a, negative pneumatic line 46 is provided with a second pressure sensor 38b, first reference chamber 28a is provided with a third pressure sensor 38c, while second reference chamber 28a is provided with a fourth pressure sensor 38d. Pressure sensors 38a to 38d output to control unit 30 as indicated by short dashed lines extending therefrom. Dashed lines extending from pneumatic pump 27, reference chambers 28a and 28b, control unit 30, user interface 40 and pneumatic valves 58 indicate electrical control and/or signal communication with control unit 30.

A pumping gasket 60 is attached to the outside of pneumatic manifold 50 and is illustrated detached in FIG. 1 from the pneumatic manifold to aid its description. Pumping gasket 60 is in one embodiment made of rubber, such as silicone rubber. Pumping gasket 60 covers pumping chambers or areas 52 and valve channels or areas 56 of pneumatic manifold 50 and moves at those areas according to negative or positive pneumatic pressure applied at those areas. Negative pneumatic pressure pulls pumping gasket at the respective area in towards pneumatic manifold 50, while positive pneumatic pressure pushes pumping gasket at the respective area outwardly from pneumatic manifold 50. Pumping gasket 60 in the illustrated embodiment includes a pre-domed pumping chamber or area 62, which helps the gasket perform a full pump stroke without having to stretch as much in comparison with a flat pumping chamber or area. Pumping gasket 60 also includes valve areas 66 that operate with corresponding valve channels or areas 56 of pneumatic manifold 50. Pumping gasket 60 may further include apertures 68, for example an aperture for each pump and valve area, which allows negative pressure from manifold 50 to extend through gasket 60 to help suck the sheeting of cassette 100 onto pumping gasket 60.

Disposable cassette 100 in the illustrated embodiment includes a rigid molded plastic piece 102 that seals on each side to cassette sheeting 104 and cassette sheeting 106. Cassette sheeting 104 and cassette sheeting 106 may be made of a thin polymer film such as polyvinyl chloride ("PVC"). Cassette sheeting 104 and cassette sheeting 106 are solvent bonded, heat sealed or ultrasonically welded to rigid plastic piece 102. Cassette sheeting 104 in the illustrated embodiment includes a pre-domed fluid pump areas 108, which mates to and matches with pre-domed pumping chambers or areas 62 of pumping gasket 60. Cassette sheeting 104 further includes valve areas 110 that mate with valve areas 66 of pumping gasket 60. Rigid piece 102 of disposable cassette defines valve chambers, e.g., volcano valve chambers (not illustrated) that operate with valve areas 110 of cassette sheeting 104 to allow or disallow fluid flow through the valve chamber. Rigid piece 102 of disposable cassette also defines fluid pump chambers 112 that operate with pre-domed fluid pump areas 108 of cassette sheeting 104 to draw fluid into or expel fluid from disposable cassette 100. Disposable cassette 100 is fluidly communicated with, e.g., attached to, fluid lines (not illustrated), such as a heater bag line, drain line, patient line, and fluid supply lines.

Conditioning Routine

During treatment when medical fluid delivery machine 20 pneumatically actuates disposable cassette 100, it is intended for pumping gasket 60 of pneumatic manifold 50 to be mated to and act as one with cassette sheeting 104 of disposable cassette 100. Due to imperfections in either pumping gasket 60 or cassette sheeting 104 and/or to misalignment of disposable cassette 100 against pumping gasket 60, the seal between cassette sheeting 104 and pumping gasket 60 may not be good enough to allow treatment to be performed. In an embodiment, control unit 30 performs a dry integrity test which evaluates the seal between cassette sheeting 104 and pumping gasket 60, e.g., via a leak rate evaluation. If the dry integrity test fails, disposable cassette 100 along with the remainder of the disposable set (lines and heater bag) has to be discarded. To reduce the failure rate of the dry integrity test due to an improper seal between cassette sheeting 104 and pumping gasket 60, the following conditioning routine has been developed.

Referring now to FIGS. 2 to 6, one embodiment of a conditioning routine stored in memory 34 and operated by processor 32 of control unit 30 is illustrated. The figures show a representation of overlaid pumping chambers or areas 52 of pneumatic manifold 50, pre-domed pumping chambers or areas 62 of pumping gasket 60, pre-domed fluid pump areas 108 of sheeting 104 and fluid pump chambers 112 of rigid piece 102. The figures also show first reference chamber 28a operating with the first pump chamber 52, 62, 108, 112 and second reference chamber 28b operating with the second pump chamber 52, 62, 108, 112.

FIGS. 2 to 6 also illustrate that in one embodiment, electrically actuated pneumatic valves 58 are provided as follows: (i) HV_HP for controlling fluid flow to and from a heater, (ii) HV_DP for controlling fluid flow to a drain, (iii) HV_PP for controlling fluid flow to and from a patient, (iv) V_nVnt1 for controlling air flow to a vent from a first reference chamber, (v) V_FMS1 for controlling air flow between the first reference chamber and a first pump chamber, (vi) V_Neg1 for controlling negative pneumatic pressure between a negative pneumatic storage tank and the first pump chamber, (vii) V_Pos1 for controlling positive pneumatic pressure between a positive pneumatic storage tank and the first pump chamber, (viii) HV_C1T for controlling fluid flow between the first pump chamber and the heater bag or drain, (ix) HV_C1B for controlling fluid flow between the first pump chamber and the patient or supply containers, (x) HV_C2B for controlling fluid flow between a second pump chamber and the patient or supply containers, (xi) HV_C2T for controlling fluid flow between the second pump chamber and the heater bag or drain, (xii) V_Pos2 for controlling positive pneumatic pressure between the positive pneumatic storage tank and the second pump chamber, (xiii) V_Neg2 for controlling negative pneumatic pressure between the negative pneumatic storage tank and the second pump chamber, (xiv) VFMS_2 for controlling air flow between a second reference chamber and the second pump chamber, (xv) V_nVnt2 for controlling air flow to a vent from a second reference chamber, (xvi) HV_BP1 for controlling fluid flow between a first supply container and the pump chambers, (xvii) HV_BP2 for controlling fluid flow between a second supply container and the pump chambers, (xviii) HV_BP3 for controlling fluid flow between a third supply container and the pump chambers, (xix) HV_BP4 for controlling fluid flow between a fourth supply container and the pump chambers, and (xx) HV_BP5 for controlling fluid flow between a fifth supply container and the pump chambers.

Figure 2:
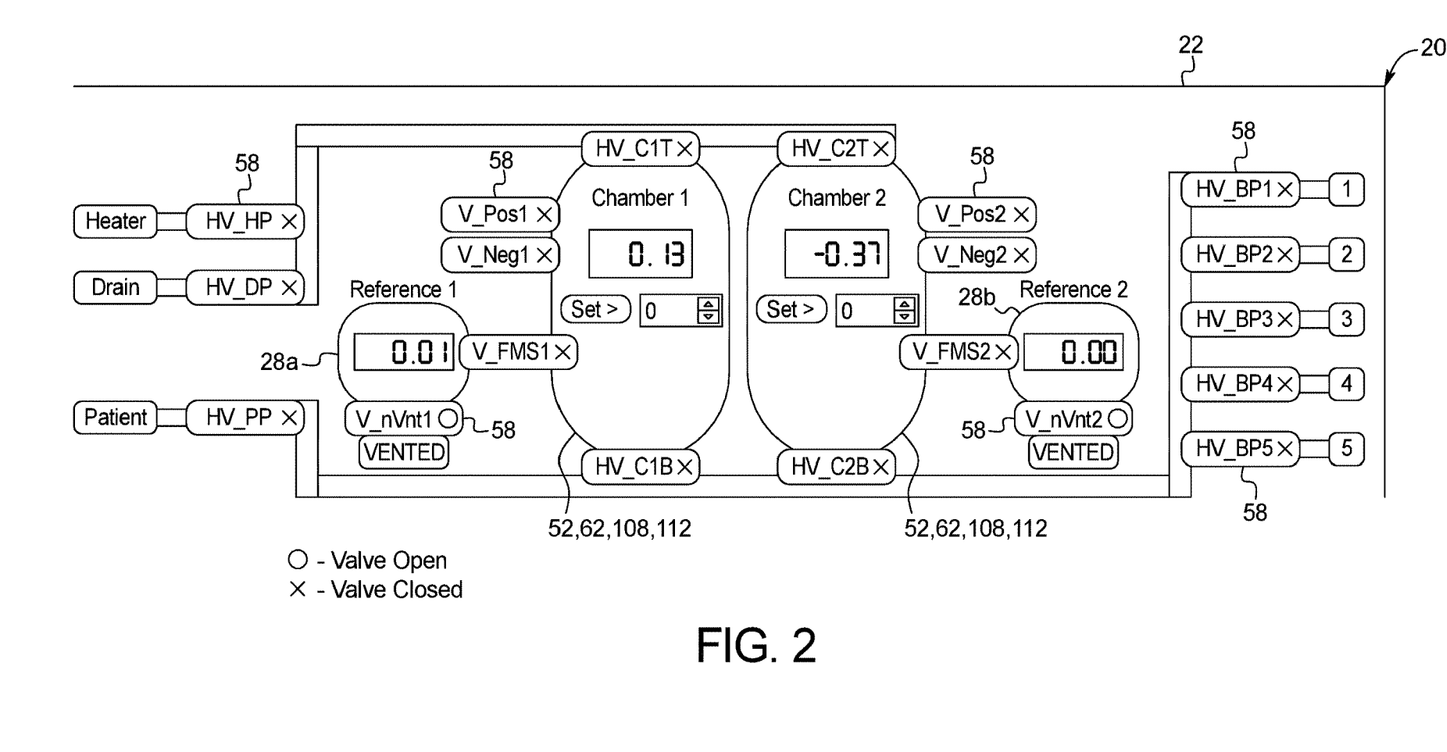
FIG. 2 is a schematic view of a first step of one embodiment of a conditioning routine of the present disclosure.

FIG. 2 illustrates a first step of one embodiment for a pumping gasket and cassette conditioning algorithm or routine stored in memory 34 and executed by processor 32 of control unit 30 of medical fluid deliver machine 20, such as a peritoneal dialysis cycler, wherein control unit causes 30 two pneumatic vent valves V_nVnt1 and V_nVnt2 to open while all other eighteen pneumatic valves are closed. This first step vents reference chambers 28a and 28b. The pressure in reference chambers 28a and 28b at the end of the first step is zero or close to zero psig. The first step sets all the valves to be at rest and readies machine 20 and disposable cassette 100 for the conditioning.

Figure 3:
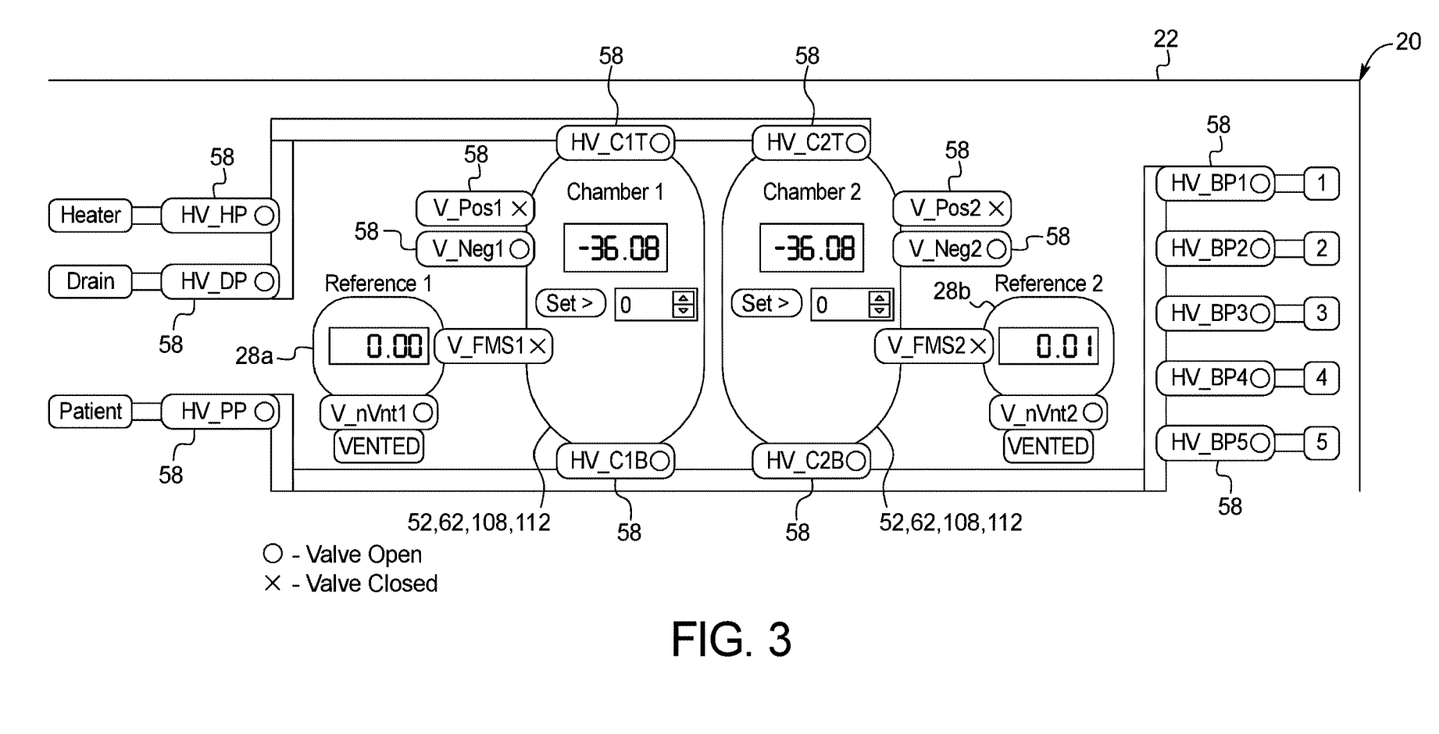
FIG. 3 is a schematic view of a second step of one embodiment of a conditioning routine of the present disclosure.

FIG. 3 illustrates a second step of one embodiment for a pumping gasket and cassette sheeting conditioning algorithm or routine, wherein control unit 30 causes all pneumatic valves 58 to open except for (i) the pneumatic valves V_Pos1 and V_Pos2 between the positive pneumatic storage tank 24 and the first and second pump chambers 52, 62, 108, 112 and (ii) the pneumatic valves V_FMS1 and V_FMS2 between the first and second pump chambers 52, 62, 108, 112 and the first and second reference chambers 28a and 28b. The two pneumatic vent valves V_nVnt1 and V_nVnt2 to reference chambers 28a and 28b are still open, so that the reference chamber pressures are still at atmospheric pressure. Pneumatic valves V_Neg1 and V_Neg2 between negative pneumatic storage tank 26 and the first and second pump chambers 52, 62, 108, 112 are opened to allow negative pressure to be applied to the pump chambers 52, 62, 108, 112 pulling pumping gasket 60 and cassette sheeting 104 together into pump chamber halves 52 defined by pneumatic manifold 50 of the machine or cycler 20. All fluid valves HV_BP1 to HV_BP5, HV_HP, HV_DP and HV_PP are opened in one implementation to allow air to flow into the disposable cassette 100 to reduce or eliminate negative pressure from building within cassette 100 that could potentially resist the movement of the cassette sheeting 104. Pumping gasket 60 and cassette sheeting 104 are thereby free to move and stretch and condition together to (i) remove small gaps or air pockets in the sealing between pumping gasket 60 and cassette sheeting 104, e.g., due to imperfections in either one or both of gasket 60 or sheeting 104 and (ii) correct misalignment between cassette 100 and pneumatic manifold 50.

Figure 4:
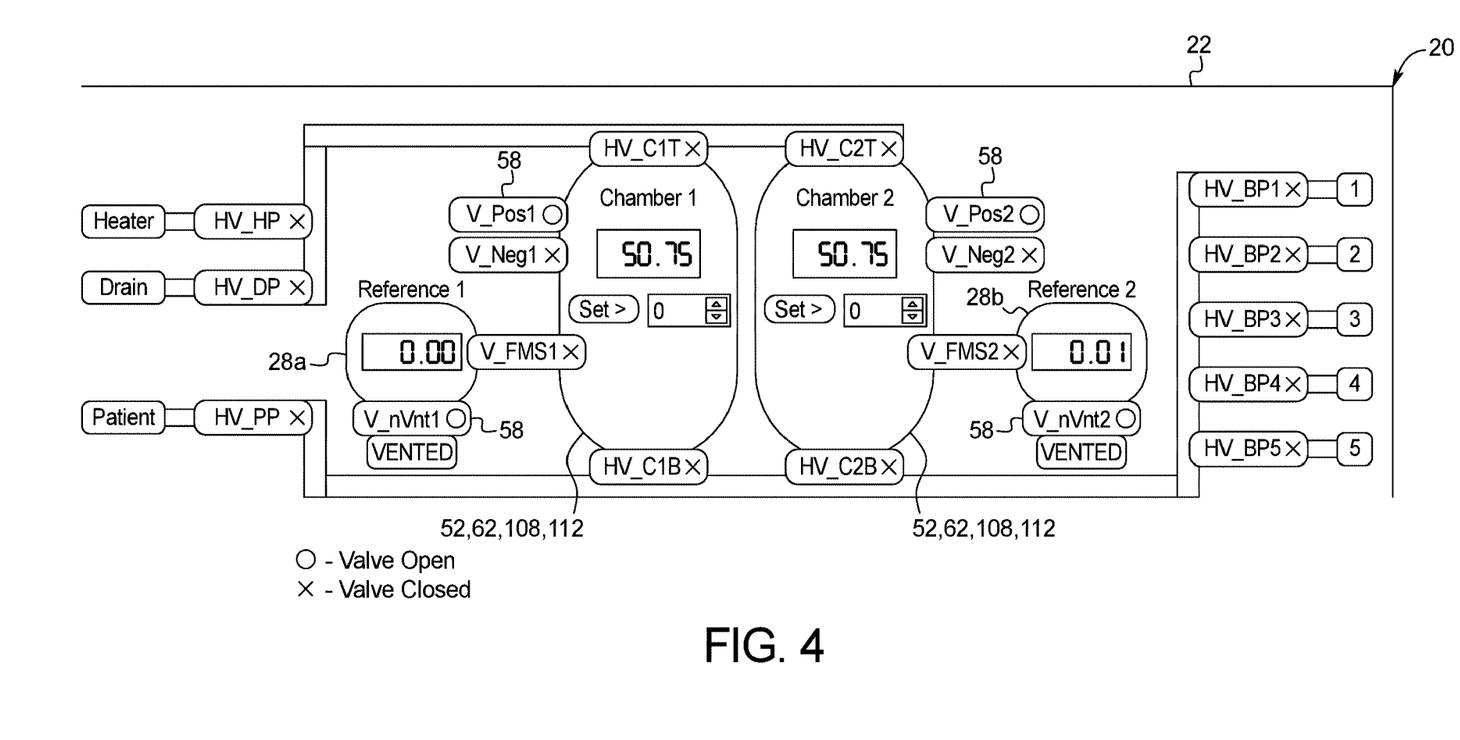
FIG. 4 is a schematic view of a third step of one embodiment of a conditioning routine of the present disclosure.

FIG. 4 illustrates a third step of one embodiment for a pumping gasket and cassette sheeting conditioning algorithm or routine, wherein control unit 30 causes all pneumatic valves 58 to be closed except for (i) pneumatic valves V_Pos1 and V_Pos2 between positive pneumatic storage tank 24 and the first and second pump chambers 52, 62, 108, 112 and (ii) the pneumatic vent valves V_nVnt1 and V_nVnt2 to reference chambers 28a and 28b, so that the reference chamber pressures are maintained at atmospheric pressure. Pneumatic valves V_Pos1 and V_Pos2 opened between positive pneumatic storage tank 24 and the first and second pump chambers 52, 62, 108, 112 allow positive pressure to be applied to the pump chambers, pushing pumping gasket 60 and cassette sheeting 104 together into fluid pump chamber halves 112 defined by disposable cassette 100. All fluid valves 58 are closed in one implementation to allow positive pressure to build inside disposable cassette 100, so that positive pressure is applied to both sides of mated pumping gasket 60 and cassette sheeting 100 to (i) squeeze air out small gaps or air pockets residing between the pumping gasket and the cassette sheeting and (ii) correct misalignment between cassette 100 and pneumatic manifold 50.

Control unit 30 having processing 32 running software in memory 34 for the conditioning routine may or may not be programmed to repeat steps two and three one or more times in various embodiments. Also, steps two and three have been described as operating the first and second pump chambers 52, 62, 108, 112 the same (pulling and pushing both simultaneously). Alternatively or additionally, pumping gasket 60 and sheeting 104 at one pump chamber 52, 62, 108, 112 may be placed under negative pressure, while the gasket and sheeting at the other pump chamber 52, 62, 108, 112 is placed under positive pressure.

Figure 5:
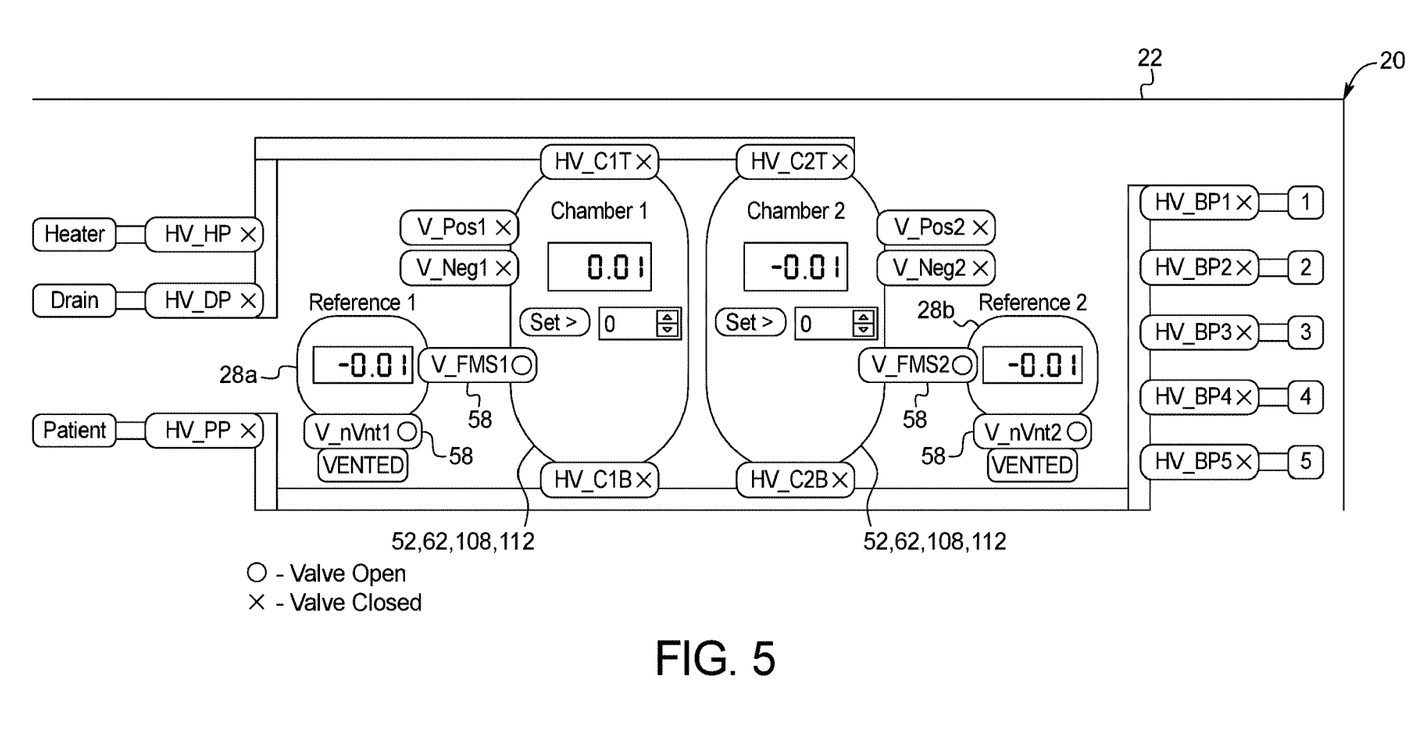
FIG. 5 is a schematic view of a fourth step of one embodiment of a conditioning routine of the present disclosure.

FIG. 5 illustrates fourth step of one embodiment for a pumping gasket and cassette sheeting conditioning algorithm or routine, wherein control unit 30 causes all pneumatic valves 58 to be closed except for (i) pneumatic valves V_FMS1 and V_FMS2 between first and second pump chambers 52, 62, 108, 112 and the first and second reference chambers 28a and 28b and (ii) the pneumatic vent valves V_nVnt1 and V_nVnt2 to the reference chambers, so that the positive pressure built in the third step is vented to atmosphere.

Figure 6:
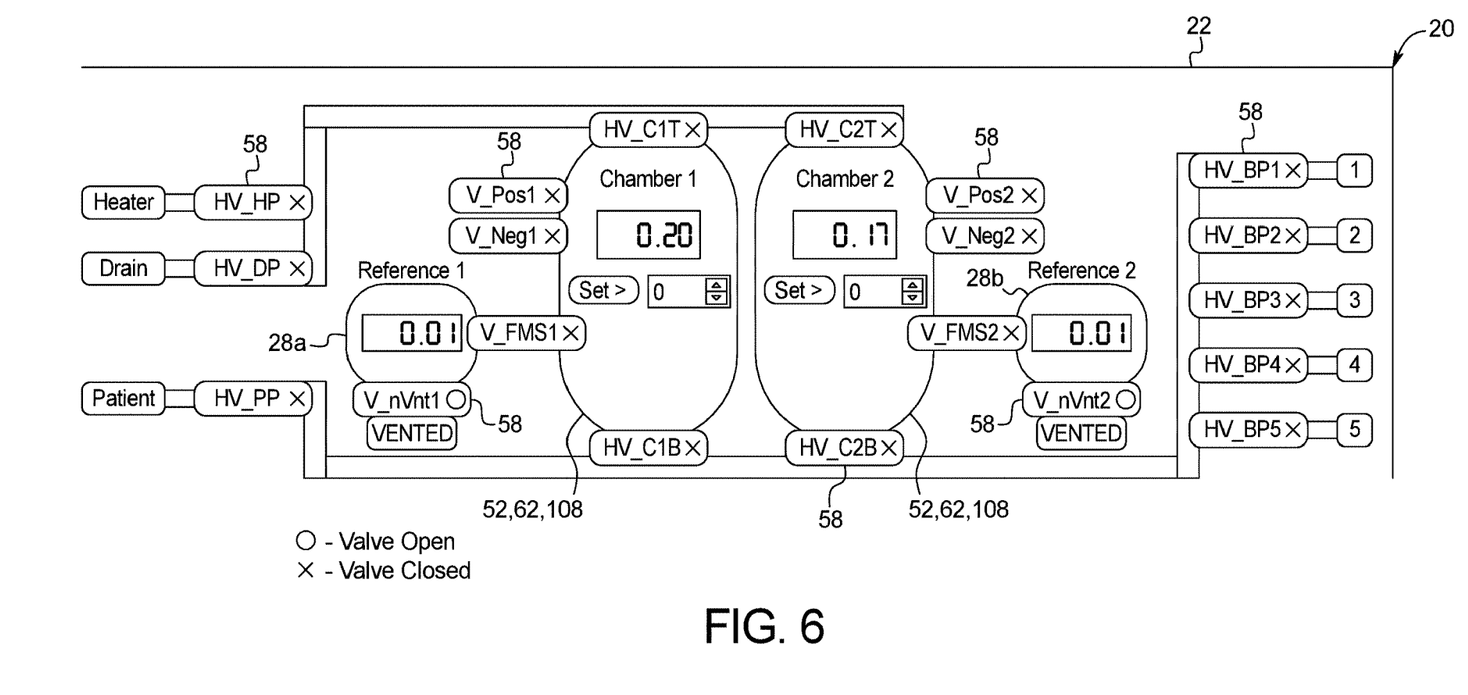
FIG. 6 is a schematic view of a fifth step of one embodiment of a conditioning routine of the present disclosure.

FIG. 6 illustrates a fourth step of one embodiment for a pumping gasket and cassette sheeting conditioning algorithm or routine, wherein control unit 30 causes the two pneumatic vent valves V_nVnt1 and V_nVnt2 to be open while all other eighteen pneumatic valves 58 are closed. This valve at rest configuration is the same as the configuration of the first step.

As mentioned above, the positive and negative pressure conditioning of pumping gasket 60 and cassette sheeting 100 may be performed either before or after a dry integrity test. For example, in one instance, the conditioning routine of FIGS. 2 to 6 is provided before the dry integrity test. Afterwards, the dry integrity test is performed.

In a second example, the conditioning routine of FIGS. 2 to 6 is provided after experiencing a dry integrity test failure. Here, control unit 60 is programmed such that after the dry integrity test failure, medical fluid delivery machine 20, such as a peritoneal dialysis cycler, prompts the patient or caregiver at user interface 40 to press a "resume" button acknowledging the dry integrity test failure. Once "resume" is pressed, control unit 30 causes the conditioning routine of FIGS. 2 to 6 described above to be performed. Afterwards, control unit 30 causes the dry integrity test to be performed again. This second example may be performed in combination with the first example or in place of the first example.

The benefits of the conditioning routine are not limited to helping with dry integrity testing. In a third example, control unit 30 causes the conditioning routine of FIGS. 2 to 6 to be performed as a result of a slow flow error (e.g., medical fluid is pumped to or from a patient too slowly despite attempting a higher flowrate). Control unit 30 is programmed such that after the slow flow error, medical fluid delivery machine 20, such as a peritoneal dialysis cycler, prompts the patient or caregiver at user interface 40 to press a "resume" button acknowledging the slow flow error. Once "resume" is pressed, the routine of FIGS. 2 to 6 is performed. Afterwards, the treatment resumes at machine 20 with hopefully a better seal between the pumping gasket 60 and the cassette sheeting 104. This third example may be performed in combination with either one or both the first example and/or the second example.

Other errors or alerts that may be aided by the conditioning routine of the present disclosure include any that involve actuation of the pumping gasket and the cassette sheeting. It should be appreciated that in any of the situations in which the conditioning routine of FIGS. 2 to 6 is performed in response to an error or alert, a patient or caregiver action, such as the pressing of a "resume" button at user interface 40, is not necessary. For example, if therapy is performed at night while the patient sleeps, it may be desirable not to wake the patient and instead perform the conditioning steps of FIGS. 2 to 6 automatically.

Figure 7:
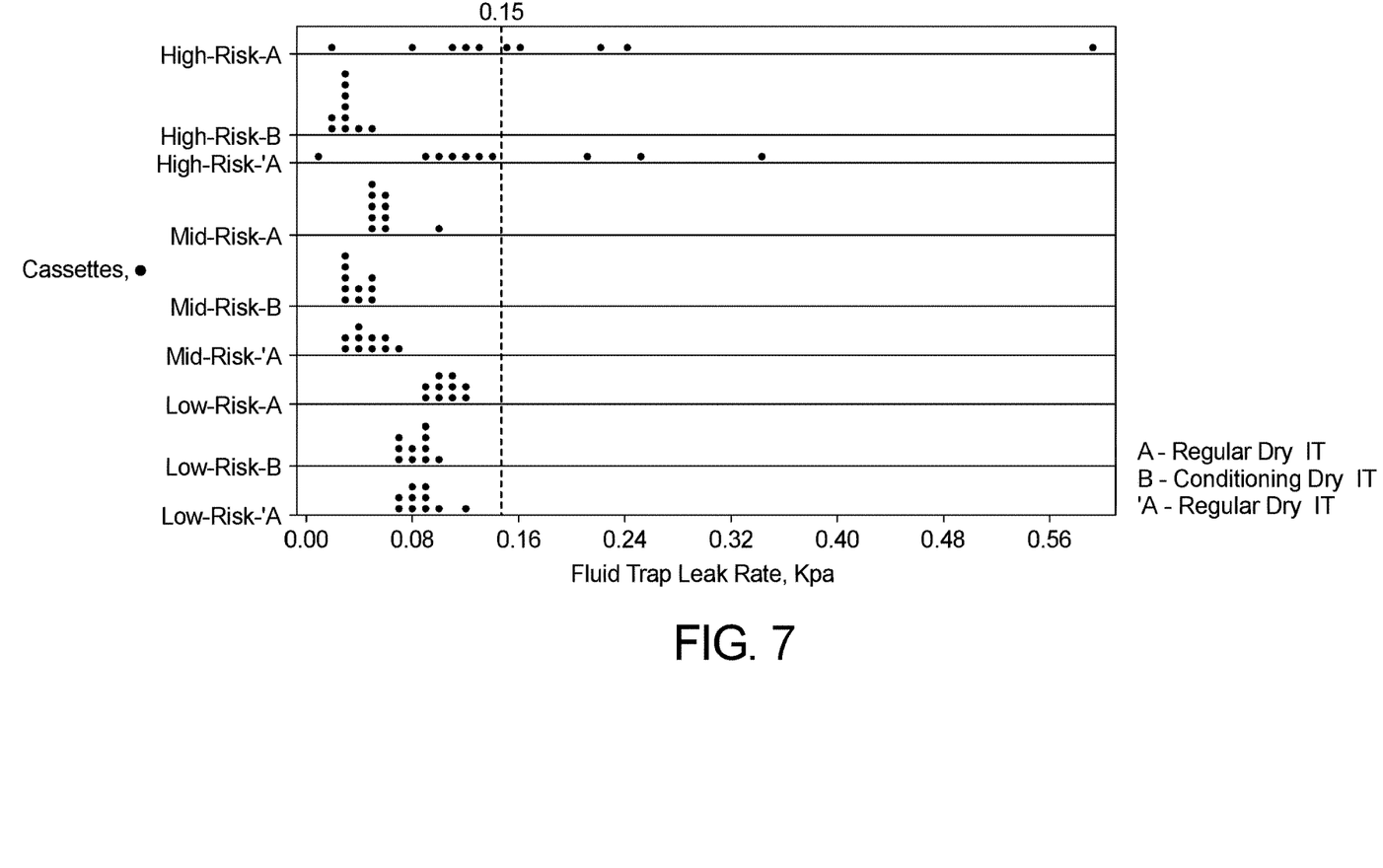
FIG. 7 is a plot of results from the conditioning routine of FIGS. 2 to 6 employed using the system of FIG. 1.

FIG. 7 illustrates a plot of pumping gasket 60 and cassette sheeting 104 sealing performance as measured by fluid leak rate of a dry leak integrity test in kilopascals ("Kpa"), wherein a leak rate of over 0.15 Kpa is considered a failure. All "A" cassette tests were performed without any conditioning routine of the present disclosure. All "B" cassette tests were performed after the conditioning routine of FIGS. 2 to 6. The tests were performed using different grades of cassette sheeting 104, wherein high risk cassettes 100 have more imperfections, middle risk cassettes 100 have less imperfections, and middle risk cassettes 100 have few imperfections. As illustrated, high risk "A" cassettes showed failures, while high risk "B" cassettes all passed. Middle risk and low risk "A" cassettes had no failures, however, middle risk and low risk "B" cassettes each had lower leak rates overall than the "A" cassettes.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims. For example, while the conditioning routine of FIGS. 2 to 6 describes applying negative pressure before the positive pressure, the reverse could be applied alternatively. Again, there may be multiple pull and push cycles or multiple push and pull cycles. Pumping chambers pump chambers 52, 62, 108, 112 may be actuated the same simultaneously, differently simultaneously, the same at different times (e.g., pull first pump chamber, then pull second pump chamber, then push first pump chamber, then push second pump chamber), or differently at different times (e.g., pull first pump chamber, then push second pump chamber, then push first pump chamber, then pull second pump chamber). Moreover, any of the different conditioning routine actuations may be combined to form an overall conditioning routine.

The invention is claimed as follows:

1. A medical fluid delivery system comprising:
   a medical fluid delivery machine including
      a pneumatic manifold having a pump actuation area, a valve actuation area, and a pumping gasket overlaying the pump and valve actuation areas,
      a vent valve pneumatically connected to a reference chamber,
      a first pneumatic valve located between a source of positive pneumatic pressure and the pump actuation area,
      a second pneumatic valve located between a source of negative pneumatic pressure and the pump actuation area,
      a third pneumatic valve located between the pump actuation area and the reference chamber, and
      a control unit in operable communication with the pneumatic valves; and
   a disposable cassette including a fluid pump chamber that aligns with the pump actuation area when the disposable cassette is mated with the pneumatic manifold, the disposable cassette including cassette sheeting configured to overlay the fluid pump chamber, wherein
   the control unit is configured to operate the pneumatic valves to perform a conditioning routine that moves the pumping gasket and the cassette sheeting while mated to remove air pockets that are located between the pumping gasket and a side of the cassette sheeting that is opposite from the fluid pump chamber by:
      (i) causing the vent valve to open to vent the reference chamber causing a pressure in the reference chamber to be approximately zero psig,
      (ii) causing the third pneumatic valve to close and the second pneumatic valve to open, thereby applying negative pneumatic pressure to the pumping gasket and the cassette sheeting while fluid valves of the disposable cassette are open,
(iii) causing the second pneumatic valve to close and the first pneumatic valve to open, thereby applying positive pneumatic pressure to the pumping gasket and the cassette sheeting while the fluid valves of the disposable cassette are closed,
(iv) causing the first pneumatic valve to close and the third pneumatic valve to open, thereby venting the positive pneumatic pressure within the pump actuation area, and
(v) causing the third pneumatic valve to close while keeping the vent valve open.

2. The medical fluid delivery system of claim 1, wherein the control unit is further configured to perform an integrity test to determine if the pumping gasket and the cassette sheeting are adequately sealed together, and wherein the conditioning routine is performed prior to the integrity test.

3. The medical fluid delivery system of claim 1, wherein the control unit is further configured to perform an integrity test to determine if the pumping gasket and the cassette sheeting are adequately sealed together, and wherein the conditioning routine is performed after a failure of the integrity test.

4. The medical fluid delivery system of claim 3, wherein the control unit is further configured to perform a second integrity test after the conditioning routine is performed.

5. The medical fluid delivery system of claim 1, wherein the control unit is further configured to detect a flow error, and wherein the conditioning routine is performed after the detection of the flow error.

6. The medical fluid delivery system of claim 1, wherein the pump actuation area is a first pump actuation area and the fluid pump chamber is a first fluid pump chamber, wherein the pneumatic manifold includes a second pump actuation area that mates with a second fluid pump chamber, and wherein the conditioning routine includes (i) applying the negative pneumatic pressure to the first and second pump actuation areas and the first and second fluid pump chambers simultaneously, and (ii) applying the positive pneumatic pressure to the first and second pump actuation areas and the first and second fluid pump chambers simultaneously.

7. The medical fluid delivery system of claim 1, wherein the pump actuation area is a first pump actuation area and the fluid pump chamber is a first fluid pump chamber, wherein the pneumatic manifold includes a second pump actuation area that mates with a second fluid pump chamber, and wherein the conditioning routine includes applying the negative pneumatic pressure to the first pump actuation area and the first fluid pump chamber while applying the positive pneumatic pressure to the second pump actuation area and the second fluid pump chamber.

8. The medical fluid delivery system of claim 1, wherein the pumping gasket and the cassette sheeting are pre-domed towards the pump actuation area.

9. A medical fluid delivery system comprising:
a medical fluid delivery machine including
a pneumatic manifold having a pump actuation area and a pumping gasket overlaying the pump actuation area,
a source of negative pneumatic pressure, and
a source of positive pneumatic pressure; and
a disposable cassette including a fluid pump chamber that aligns with the pump actuation area when the disposable cassette is mated with the pneumatic manifold, the disposable cassette including cassette sheeting overlaying the fluid pump chamber,
wherein the medical fluid delivery machine is configured to perform a conditioning routine that includes:
at a first time, placing the pumping gasket and the cassette sheeting overlaying the fluid pump chamber under negative pressure from the source of negative pneumatic pressure, and
at a second time, placing the pumping gasket and the cassette sheeting overlaying the fluid pump chamber under positive pressure from the source of positive pressure, thereby moving the pumping gasket and the cassette sheeting while mated in two directions to remove air pockets between the pumping gasket and a side of the cassette sheeting that is opposite from the fluid pump chamber, wherein the conditioning routine is performed (i) prior to or in response to a result of a disposable cassette installation test, or (ii) in response to a treatment error or alert.

10. The medical fluid delivery system of claim 9, wherein the disposable cassette installation test includes a dry integrity test.

11. The medical fluid delivery system of claim 9, wherein the treatment error or alert includes a flow error.

12. The medical fluid delivery system of claim 9, wherein the medical fluid delivery machine is configured to perform the conditioning routine by pneumatically pulling the pumping gasket and the cassette sheeting in a first one of the two directions and by pneumatically pushing the pumping gasket and the cassette sheeting in a second one of the two directions.

13. The medical fluid delivery system of claim 12, wherein the disposable cassette is in fluid communication with a plurality of fluid lines, and wherein the fluid lines are open when pneumatically pulling the pumping gasket and the cassette sheeting and occluded when pneumatically pushing the pumping gasket and the cassette sheeting.

14. The medical fluid delivery system of claim 9, wherein the pumping gasket includes at least one aperture positioned and arranged to enable the negative pneumatic pressure to be applied through the at least one aperture to pull the cassette sheeting against the pumping gasket.

15. The medical fluid delivery system of claim 9, wherein the medical fluid delivery machine includes a control unit, the control unit configured to cause the conditioning routine to be performed.

16. A method for a medical fluid delivery machine including a source of negative pneumatic pressure, a source of positive pneumatic pressure, and a pneumatic manifold having a pump actuation area and a pumping gasket, overlaying the pump actuation area, that mates with cassette sheeting of a disposable cassette when the disposable cassette is mounted to the medical fluid delivery machine, the method comprising:
conditioning the pumping gasket and the cassette sheeting when mated by moving the pumping gasket and the cassette sheeting together to remove air pockets between the pumping gasket and an external side of the cassette sheeting, wherein conditioning the pumping gasket includes:
at a first time, placing the pumping gasket and the cassette sheeting overlaying a fluid pump chamber under negative pressure from the source of negative pneumatic pressure, wherein the fluid pump chamber aligns with the pump actuation area when the disposable cassette is mated with the pneumatic manifold, and at a second time, placing the pumping gasket and the cassette sheeting overlaying the fluid pump chamber under positive pressure from the source of positive pressure; and performing an integrity test on the pumping gasket and the cassette sheeting to evaluate how well the cassette sheeting is sealed to the pumping gasket.

17. The method of claim 16, wherein conditioning includes moving the pumping gasket and the cassette sheeting back and forth at least one time.

18. The method of claim 16, further comprising conditioning the pumping gasket and the cassette sheeting again after at least one of: (i) a failure of the integrity test, or (ii) a flow error during a treatment provided by the medical fluid delivery machine and the disposable cassette.

* * * * *